US011655202B2

(12) United States Patent
Meyer et al.

(10) Patent No.: US 11,655,202 B2
(45) Date of Patent: May 23, 2023

(54) PROCESS FOR PREPARING A CYCLOALIPHATIC DIESTER

(71) Applicant: COVESTRO INTELLECTUAL PROPERTY GMBH & CO. KG, Leverkusen (DE)

(72) Inventors: Alexander Meyer, Düsseldorf (DE); Thomas Pfingst, Tönisvorst (DE); Dirk Hinzmann, Pulheim (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 0 days.

(21) Appl. No.: 17/268,991

(22) PCT Filed: Aug. 14, 2019

(86) PCT No.: PCT/EP2019/071779
§ 371 (c)(1),
(2) Date: Feb. 17, 2021

(87) PCT Pub. No.: WO2020/035519
PCT Pub. Date: Feb. 20, 2020

(65) Prior Publication Data
US 2022/0119334 A1   Apr. 21, 2022

(30) Foreign Application Priority Data

Aug. 17, 2018 (EP) .................... 18189636

(51) Int. Cl.
*C07C 67/10* (2006.01)
*C08G 64/20* (2006.01)
*C08G 63/64* (2006.01)
*C07C 69/75* (2006.01)

(52) U.S. Cl.
CPC ............ *C07C 67/10* (2013.01); *C07C 69/75* (2013.01); *C08G 63/64* (2013.01); *C08G 64/20* (2013.01)

(58) Field of Classification Search
CPC .......... C07C 67/10; C07C 69/75; C08G 64/20
See application file for complete search history.

(56) References Cited

U.S. PATENT DOCUMENTS

| 3,453,341 A | * | 7/1969 | Bushick | ................ C07C 5/2721 585/360 |
| 7,781,540 B2 | * | 8/2010 | Yanagida | .............. C08L 67/025 528/196 |
| 2001/0018162 A1 | * | 8/2001 | Hatakeyama | ......... G03F 7/0397 430/326 |
| 2002/0137877 A1 | * | 9/2002 | Debruin | ................ B01J 8/0035 528/272 |
| 2011/0223525 A1 | * | 9/2011 | Sacripante | ......... G03G 9/08797 430/105 |
| 2019/0071532 A1 | * | 3/2019 | Strand | ................ C08G 18/7671 |

FOREIGN PATENT DOCUMENTS

| EP | 1609818 A2 | 12/2005 | |
| EP | 3026074 A1 | 6/2016 | |
| EP | 3248999 A1 | 11/2017 | |
| JP | 07-126213 A | 5/1995 | |
| WO | 02/10111 A1 | 2/2002 | |
| WO | WO-0210111 A1 * | 2/2002 | ............. C07C 67/10 |
| WO | WO-2015012619 A1 * | 1/2015 | ............. C08G 63/64 |
| WO | WO-2016117872 A1 * | 7/2016 | ............. C08G 63/64 |

OTHER PUBLICATIONS

International Preliminary Report on Patentability received for PCT Patent Application No. PCT/EP2019/071779, dated Mar. 4, 2021, 12 pages (6 pages of English Translation and 6 pages of Original Document).
International Search Report and Written Opinion received for PCT Patent Application No. PCT/EP2019/071779, dated Oct. 30, 2019, 12 pages. (6 pages of English Translation and 6 pages of Original Document).

* cited by examiner

*Primary Examiner* — Yate' K Cutliff
(74) *Attorney, Agent, or Firm* — The Webb Law Firm

(57) ABSTRACT

The present invention relates to a method for producing a cycloaliphatic diester, to a method for producing a polyestercarbonate using the one cycloaliphatic diester, to the use of a cycloaliphatic diester for producing polyestercarbonates and also to a polyestercarbonate. The method according to the invention is here in particular characterized in that the cycloaliphatic diester is separated by means of distillation from the reaction mixture.

18 Claims, No Drawings

PROCESS FOR PREPARING A CYCLOALIPHATIC DIESTER

CROSS-REFERENCE TO RELATED APPLICATIONS

This application is a national stage application (under 35 U.S.C. § 371) of PCT/EP2019/071779, filed Aug. 14, 2019, which claims benefit of European Application No. 18189636.6, filed Aug. 17, 2018, both of which are incorporated herein by reference in their entirety.

The present invention relates to a method for producing a cycloaliphatic diester, to a method for producing a polyestercarbonate using a cycloaliphatic diester, to the use of a cycloaliphatic diester for producing polyestercarbonates and also to a polyestercarbonate.

It is known that polyesters, polycarbonates and polyestercarbonates have good properties with regard to mechanical properties, heat distortion resistance and weathering stability. Depending on the monomers used, each polymer group has certain key features that distinguish materials of this type. For instance, polycarbonates in particular have good mechanical properties, whereas polyesters often display better chemical stability. Polyestercarbonates, depending on the monomers selected, display property profiles from both of said groups.

Although aromatic polycarbonates or polyesters do often have a good property profile, they exhibit weaknesses in terms of ageing and weathering stability. For example, absorption of UV light leads to yellowing and possibly embrittlement of these thermoplastic materials. Aliphatic polycarbonates and polyestercarbonates in this respect have better properties, especially better ageing and/or weathering stability. A further advantage of aliphatic polymers is the improved accessibility to the raw materials in respect of bioavailability. Aliphatic monomers such as succinic acid or isosorbide are today available from bio-based raw materials, whereas in contrast the aromatic monomers are available only to a limited extent, if at all, from bio-based raw materials. In the context of the present invention, the expression "bio-based" is understood to mean that the relevant chemical compound at the filing date is available and/or obtainable via a renewable and/or sustainable raw material, and/or preferably is such a renewable and/or sustainable raw material. The expression serves in particular for demarcation with respect to raw materials from fossil raw materials. Whether a raw material is bio-based or based on fossil raw materials can be determined by measurement of carbon isotopes in the raw material, as the relative amounts of the carbon isotope C14 are lower in fossil raw materials. This can be done, for example, in accordance with ASTM D6866-18 (2018) or ISO16620-1 to -5 (2015).

The drawback with aliphatic polycarbonates or polyestercarbonates is often the low glass transition temperature thereof. Accordingly, it is advantageous to use cycloaliphatic alcohols as (co)monomers. Examples of such cycloaliphatic alcohols are TCD alcohol (tricyclodecanedimethanol), cyclohexanediol, cyclohexanedimethanol and bio-based diols based on 1,4:3,6-dianhydrohexitols such as isosorbide and the isomers isomannide and isoidide. In order to increase the glass transition temperature further, cycloaliphatic acids such as cyclohexane-1,2-, -1,3- or -1,4-dicarboxylic acids can also be used as (co)monomers. Depending on the choice of the reactants, polyesters or polyestercarbonates are then obtained. The polyesters of cyclohexanedicarboxylic acid and isosorbide are described by Oh et al. in Macromolecules 2013, 46, 2930-2940. However, the present invention is preferably targeted towards polyestercarbonates.

Yet polyestercarbonates are not industrially producible from the free acids, but are produced by transesterification of corresponding ester-containing monomers with diols. For instance, the polyester of cyclohexane-1,4-dimethanol and cyclohexane-1,4-dicarboxylic acid is produced starting from the dimethyl ester of the diacid (blend of this polyester and polycarbonate: Xyrex from DuPont).

However, the reactivity of these ester-containing monomers of cycloaliphatic acids plays a large role in the later polymerization by means of transesterification. There has not been a lack of attempts to date to produce such cycloaliphatic diesters, which are suitable in particular for the production of polyestercarbonates. It is known that phenyl esters of this kind display a markedly higher reactivity in transesterification reactions than do their aliphatic analogues. This has been described, for example, in EP 3026074 A1 and in EP 3248999 A1.

In these documents the production of diphenyl esters has also been described. In EP 3026074 A1, the direct reaction of the diacid with phenol to give the corresponding ester is described (Example 1). However, the yield in the synthesis steps with respect to the phenyl ester is rather low (Example 1: EP3026074). In Example 2 of EP 3026074 A1, a dimethyl ester is reacted with phenol. Here too, the yield of the diphenyl ester is capable of improvement.

Example 1 and Example 2 of EP3248999 A1 describe the use of solvents for the production of the diphenyl ester and require feedstocks such as phosgene which are not easy to handle. The use of solvents makes the method expensive, since the solvents have to be removed on completion of the reaction, which neither is energetically favourable nor can be judged positively from environmental points of view. The use of phosgene not only requires high levels of safety precautions but is also expensive overall. Since the subsequent reaction to give the aliphatic polyestercarbonate does without phosgene, the combination of a phosgene process with a transesterification process in one part of a plant is very disadvantageous. Therefore, the methods described in EP 3026074 A1 and in EP 3248999 A1 are not optimal.

In WO2002/10111 A1, a method for producing an aliphatic diphenyl ester is described in which an aliphatic, linear diacid is reacted with diphenyl carbonate. This is followed by a purification of the diester via recrystallization using solvents. These too, as described above, must subsequently be removed again. In addition, this document does not contain any example in which cycloaliphatic diacids are used (instead exclusively linear diacids). In contrast to linear diacids, cycloaliphatic diacids are in most cases more unstable. By way of example, thermogravimetric analysis on cyclohexane-1,4-dicarboxylic acid already shows at 200° C. a first loss of weight. The reaction conditions of linear diacids are thus not readily transposable to cycloaliphatic diacids. Those skilled in the art would especially avoid thermal stresses on cycloaliphatic diacids.

In JP H07-126213, the reaction of an aromatic diacid such as terephthalic acid or isophthalic acid with a diaryl carbonate is described. Such aromatic diacids have a very high thermal stability. For this reason, the reaction conditions of aromatic diacids are likewise not readily transposable to cycloaliphatic diacids.

The present invention was therefore based on the object of providing a method for producing a cycloaliphatic diester which rectifies at least one disadvantage of the prior art. In particular, the present invention was based on the object of providing a method in which the use of phosgene is not necessary. Moreover, a method is intended to be provided which can be conducted in a solvent-free manner. In this case, though, the cycloaliphatic diester is intended to be able to be obtained in a simple manner without a high loss of yield, for example by thermal decomposition, and preferably with high purity.

At least one, preferably all of the abovementioned objects were achieved by the present invention. Surprisingly, it was found that the direct reaction of a cycloaliphatic dicarboxylic acid with at least one aliphatic and/or aromatic carbonate in the presence of a basic catalyst leads to the desired product, and that this product can be obtained with high purity and also high yield by means of subsequent distillation. This was especially surprising, since it could not be assumed that the cycloaliphatic diester would be readily distillable. In addition, with a distillation the product of residence time and temperature is considerably increased with respect to a recrystallization. It could therefore not be assumed that a cycloaliphatic diester would endure the thermal stresses according to the invention without serious losses of yield. Those skilled in the art would have rather expected that the thermal stress would firstly lead to decomposition, which reduces the yield, and with it secondly to additional by-products, which contaminate the target product. It was moreover found that for transesterification the activation of the dicarboxylic acid, for example by the production of the corresponding acid chloride, is not necessary. The acid chloride is produced, by way of example, via thionyl chloride or phosgene—both sterically less-demanding and highly reactive substances, which are accompanied by the above-described disadvantages such as the use of solvents. In contrast, an aliphatic or aromatic carbonate, for example diphenyl carbonate, is rather slow to react and, especially compared to phosgene, sterically more demanding. Since the cycloaliphatic ring alone makes the carboxylic acid sterically more difficult to attack—in particular compared to linear carboxylic acids—the reaction with the likewise sterically demanding diaryl carbonate was extremely surprising.

In this way, a method for producing a cycloaliphatic diester could thus be discovered which does not require the use of phosgene and as a result is not associated with corresponding safety precautions. Moreover, the method can be conducted in a solvent-free manner. This makes the method according to the invention environmentally friendly. Since a distillation is additionally relatively uncomplicated, a corresponding workup can also be used in already existing industrial plants. It should be ensured here that, during the reaction, the phenol forming is removed by distillation in order to shift the equilibrium of the reaction. In the same apparatus, it would subsequently be possible to distil off the desired product. The method according to the invention thus also offers corresponding advantages for the plant construction.

A further advantage of the method according to the invention is also to be seen in the fact that the cycloaliphatic diester is intended to subsequently be reacted via a melt transesterification process to give a polyestercarbonate. Since this reaction already the melting of the compound and thus is associated with an input of energy, the product of the method according to the invention that is distilled off can be supplied directly to this transesterification process. In this case a corresponding remelting is then not necessary as by means of the distillation of the cycloaliphatic diester there was already a corresponding input of energy. Thus, on the whole, an overall method can be designed which comprises the production of the monomer and the subsequent polymerization, and which is particularly advantageous in terms of economic and ecological aspects.

In addition, it has surprisingly been found that the process product of the method according to the invention yields a monomer that can be converted into a polyestercarbonate which has particularly advantageous properties. It has especially been found that, when using the cycloaliphatic diester according to the invention, polyestercarbonates which have a particularly good intrinsic inherent colour are accessible according to the invention. This colour is in particular better than a polyestercarbonate that was produced in a reaction with a cycloaliphatic diester that had not been purified further. It is evident from this that the distillation process removes different by-products and/or impurities from the product than the recrystallization.

According to the invention, therefore, a method for producing a cycloaliphatic diester of formula (Ia) or (Ib) is provided,

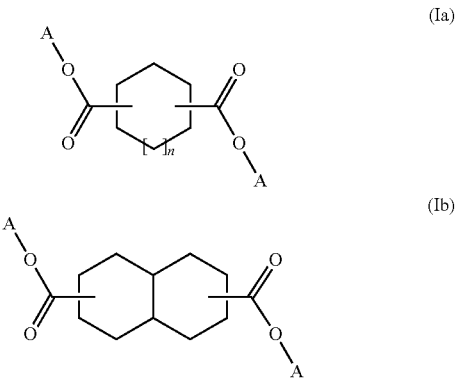

in which

A each independently is an aliphatic or aromatic radical, preferably having 1 to 10 carbon atoms, particularly preferably an optionally substituted aromatic radical, very particularly preferably a substituted or unsubstituted phenyl group and n is a number between 0 and 3, preferably 0 or 1, comprising the steps of
(i) reacting a mixture comprising at least one cycloaliphatic dicarboxylic acid and at least one aliphatic and/or aromatic carbonate, in the presence of a basic catalyst, to give a cycloaliphatic diester of formulae (Ia) or (Ib) and
(ii) separating the cycloaliphatic diester of formula (Ia) or (Ib) from the mixture of method step (i) by means of distillation.

It is further preferred here according to the invention that in formula (Ia) or (Ib) both instances of A are the same. It is additionally preferred for them to be a substituted or unsubstituted phenyl group, particularly preferably an unsubstituted phenyl group.

It is also preferred that in formula (Ia) n is 0 or 1.

Step (i) of the method according to the invention comprises reacting a mixture comprising at least one cycloaliphatic dicarboxylic acid and at least one aliphatic and/or aromatic carbonate, in the presence of a basic catalyst, to give a cycloaliphatic diester of formulae (Ia) or (Ib). This reaction shall be explained below, consistently using the reaction of a cyclohexanedioic acid with diphenyl carbonate (DPC) as an example. In spite of this, the invention is not restricted to these specific compounds, although they are preferred. Those skilled in the art are capable of applying the reaction and the corresponding explanations to others of the described compounds.

In step (i), the following (exemplary) reaction takes place:

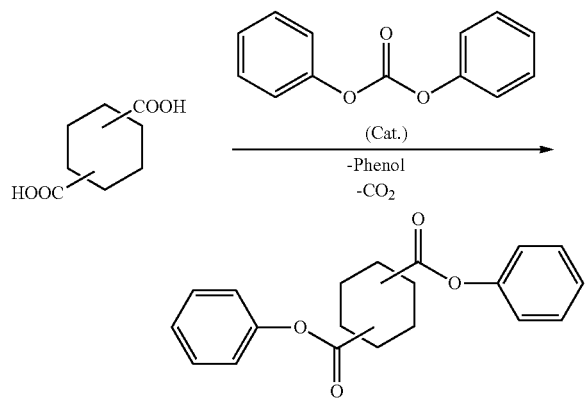

During the reaction, carbon dioxide and phenol (or a compound A-OH, where A has the meanings described with respect to formulae (Ia) and (Ib)) is thus released. It has been found to be advantageous according to the invention if this condensation product A-OH is removed during reaction step (i). Here, the expression "during step (i)" may mean that removal is begun directly at the start of method step (i) or only after a time delay after the start of step (i). Removal can be performed in a manner known to those skilled in the art, preferably by application of a reduced pressure adapted to the reaction conditions. It must be ensured here, though, that temperature and reduced pressure in method step (i) are selected such that the aliphatic and/or aromatic carbonate as reactant, and preferably initially also the cycloaliphatic diester as product, is not also removed from the reaction mixture.

In addition, the method step (i) according to the invention preferably comprises at least one, particularly preferably all, of the following steps (ia) to (id):

(ia) Melting the at least one cycloaliphatic dicarboxylic acid and the aliphatic and/or aromatic carbonate. This is preferably effected under a protective gas atmosphere, preferably under nitrogen and/or argon. As an alternative, the melting may also be effected in a vacuum.

It is preferred according to the invention that a molar excess of the at least one aliphatic and/or aromatic carbonate in relation to the at least one cycloaliphatic dicarboxylic acid is used. With particular preference, for one mole of the at least one cycloaliphatic dicarboxylic acid, 2.01 to 2.5, particularly preferably 2.05 to 2.2 mol of the at least one aliphatic and/or aromatic carbonate are used. This has the advantage in particular that a high yield can be achieved. Moreover, losses of carbonate, which possibly occur as a result of the removal of the condensation product, can be compensated.

In one aspect of the invention, one or more stabilizers can be added to the melt in method step (ia). The cycloaliphatic diester according to the invention is exposed during the reaction to great thermal stress. It is additionally preferable to conduct the entire reaction in a manner as free from oxygen as possible. Oxygen inevitably leads to the formation of oxidation products. In order to minimize this formation, stabilizers and/or antioxidants may also be used.

This at least one stabilizer is preferably selected from the group consisting of P-containing (phosphorus-containing) stabilizers and/or phenolic free-radical scavengers. Phosphites and phosphonites are preferentially suitable, as are phosphines. Examples include triphenyl phosphite, diphenyl alkyl phosphite, phenyl dialkyl phosphite, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis (2,4-di-tert-butylphenyl) pentaerythritol diphosphite, bis(2, 4-dicumylphenyl) pentaerythritol diphosphite, bis(2,6-di-tert-butyl-4-methylphenyl) pentaerythritol diphosphite, diisodecyloxy pentaerythritol diphosphite, bis(2,4-di-tert-butyl-6-methylphenyl) pentaerythritol diphosphite, bis(2,4, 6-tris(tert-butylphenyl) pentaerythritol diphosphite, tristearyl sorbitol triphosphite, tetrakis(2,4-di-tert-butylphenyl)-4,4'-biphenylenediphosphonite, 6-isooctyloxy-2,4,8, 10-tetra-tert-butyl-12H-dibenzo[d,g]-1,3,2-dioxaphosphocine, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyldibenzo [d,g]-1,3,2-dioxaphosphocine, 2,2',2"-nitrilo[triethyltris(3, 3',5,5'-tetra-tert-butyl-1,1'-biphenyl-2,2'-diyl) phosphite], 2-ethylhexyl 3,3',5,5'-tetra-tert-butyl-1,1'-biphenyl-2,2'-diyl phosphite, 5-butyl-5-ethyl-2-(2,4,6-tri-tert-butylphenoxy)-1,3,2-dioxaphosphirane, bis(2,6-di-tert-butyl-4-methylphenyl)pentaerythritol diphosphite, triphenylphosphine (TPP), trialkylphenylphosphine, bisdiphenylphosphinoethane or a trinaphthylphosphine. Especially preferably, triphenylphosphine (TPP), Irgafos® 168 (tris(2,4-di-tert-butylphenyl) phosphite) and tris(nonylphenyl) phosphite or mixtures thereof are used.

It is also possible to use phenolic free-radical scavengers such as alkylated monophenols, alkylated thioalkylphenols, hydroquinones and alkylated hydroquinones. Particularly preferably used are Irganox® 1010 (pentaerythritol 3-(4-hydroxy-3,5-di-tert-butylphenyl) propionate; CAS: 6683-19-8) and Irganox 1076@ (2,6-di-tert-butyl-4-(octadecanoxycarbonylethyl)phenol).

It is additionally advantageous to use a combination of P-containing (phosphorus-containing) stabilizer with phenolic free-radical scavengers. The combination of (tris(2,4-di-tert-butylphenyl) phosphite) with (2,6-di-tert-butyl-4-(octadecanoxycarbonylethyl)phenol) is particularly suitable.

(ib) Heating the mixture, preferably the melt obtained from step (ia). The heating is preferably effected up to 150° C. to 300° C., particularly preferably 180° C. to 280° C. and especially preferably up to 190° C. to 240° C.

(ic) Reacting the mixture, preferably the mixture obtained from step (ib), while introducing mixing energy, preferably by stirring. The reaction time in this step depends on the amount of feedstocks. The reaction time for step (ic) is with preference between 0.5 h to 24 h, preferably between 1 h and 18 h and especially preferably between 1.5 h and 10 h. The time it is preferable here to choose the reaction time such that the carbonate is almost completely reacted. The progress of the reaction can be followed, in a way known to those skilled in the art, by means of the formation of carbon dioxide (see reaction scheme above).

(id) Removal of the condensation product A-OH, preferably from the mixture obtained from step (ic). It is accordingly preferred that the method according to the invention is characterized in that, during the reaction in method step (i), the volatile constituents which have a boiling point below the cycloaliphatic diester of formula (Ia) or (Ib) and below the aliphatic and/or aromatic carbonate are removed, optionally in steps, by means of distillation.

A removal in steps is preferably selected here if different volatile constituents are being removed. A removal in steps is likewise preferably selected in order to guarantee as complete as possible a removal of the volatile constituent(s). The volatile constituents are preferably the compound A-OH, where A has the meanings described with respect to formula (Ia) and (Ib). They are preferably a substituted or unsubstituted phenol, if A is a substituted or unsubstituted phenyl group.

The condensation product is preferably removed at temperatures of 150° C. to 250° C., particularly preferably 180° C. to 230° C. The vacuum during the removal is further preferably 500 mbar to 0.01 mbar. It is especially preferred for the removal to occur in steps by reduction of the vacuum. The vacuum in the final stage is very particularly preferably 10 mbar to 0.01 mbar in order to remove phenol as condensation product.

The at least one cycloaliphatic dicarboxylic acid used in method step (i) is preferably selected from a compound of chemical formula (IIa) or (IIb):

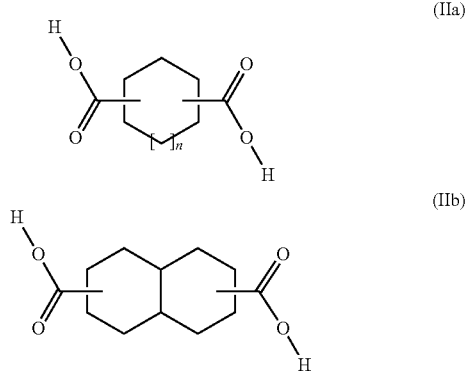

in which n is a number between 0 and 3. The preferences described for n with respect to formula (Ia) and (Ib) preferably apply.

The at least one cycloaliphatic dicarboxylic acid in method step (i) is particularly preferably selected from the group consisting of cyclohexane-1,4-dicarboxylic acid, cyclohexane-1,3-dicarboxylic acid, cyclohexane-1,2-dicarboxylic acid, decahydronaphthalene-2,4-dicarboxylic acid, decahydronaphthalene-2,5-dicarboxylic acid, decahydronaphthalene-2,6-dicarboxylic acid, decahydronaphthalene-2,7-dicarboxylic acid, very particularly preferably from cyclohexane-1,4-dicarboxylic acid, cyclohexane-1,3-dicarboxylic acid and cyclohexane-1,2-dicarboxylic acid, further preferably cyclohexane-1,4-dicarboxylic acid.

The at least one aliphatic and/or aromatic carbonate used in method step (i) is preferably at least one aromatic carbonate. Cycloaliphatic diacids that have been esterified with aliphatic alcohols display, in the transesterification reaction to give polyestercarbonates, a low reactivity than those with aromatic alcohols, and as a result the molecular weights of the corresponding polyestercarbonates after transesterification reaction are rather low. These polymers in that case display only unsatisfactory properties. Therefore, the use of aromatic carbonates is particularly advantageous for the resulting polymer properties. An aromatic carbonate of formula (2) is particularly preferably used in method step (i)

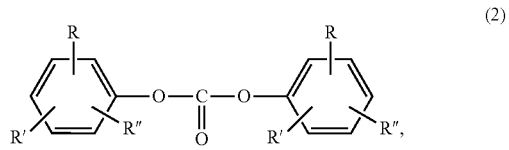

where R, R' and R" each independently can be the same or different and are hydrogen, optionally branched C1-C34-alkyl, C7-C34-alkylaryl or C6-C34-aryl, R can additionally also denote —COO—R''', where R''' is optionally branched C1-C34-alkyl, C7-C34-alkylaryl or C6-C34-aryl. Such carbonates have been described, for example, in EP-A 1 609 818. Preference is given to diphenyl carbonate, 4-tert-butylphenyl phenyl carbonate, di(4-tert-butylphenyl) carbonate, biphenyl-4-yl phenyl carbonate, di(biphenyl-4-yl) carbonate, 4-(1-methyl-1-phenylethyl)phenyl phenyl carbonate and di[4-(1-methyl-1-phenylethyl)phenyl] carbonate. Substituted or unsubstituted, preferably unsubstituted diphenyl carbonate is very particularly preferably used as aromatic carbonate in method step (i).

The carbonates may also be used with residual contents of the monohydroxyaryl compounds from which they were produced. The residual contents of the monohydroxyaryl compounds may amount to up to 20%, preferably 10%, particularly preferably up to 5% and very particularly preferably up to 2%. This means that in the method according to the invention, carbonates can also be used which do not have to be subjected to complex purification after their production process. Since, in the method according to the invention, the monohydroxyaryl compound from which the carbonate was obtained reappears as condensation product A-OH and is preferably removed, these impurities do not disturb the reaction. By means of such a favourably produced carbonate, the method according to the invention can be configured to be even more economically advantageous overall.

In another aspect, the at least one aliphatic and/or aromatic carbonate can also be produced in a phosgene-free manner. This makes it possible for the entire method for producing a polyestercarbonate to be able to be conducted in a phosgene-free manner.

It has emerged that, according to the invention, the presence of at least one basic catalyst in method step (i) is required. Otherwise, the reaction between carbonate and diacid does not take place. This proves that reaction conditions based on linear aliphatic dicarboxylic acid cannot be transposed to the conversion of cycloaliphatic dicarboxylic acids, as in WO 02/10111 A1 the reaction of DPC with linear aliphatic dicarboxylic acids at temperatures of 180° C. is described and is also preferred. It is described that reaction products which are obtained in the presence of a basic catalyst have more impurities. It has now been found, according to the invention, that in the reaction with cycloaliphatic dicarboxylic acids a catalyst is essential at least at moderate temperatures and that nevertheless products having high purity can be obtained by the method according to the invention.

The basic catalyst is a base or a basic transesterification catalyst. By way of example, the following bases or catalysts may be used here:

alkali metal compounds such as LiOH, NaOH, KOH, CsOH, $Li_2CO_3$, $Na_2CO_3$, $K_2CO_3$, $Cs_2CO_3$, LiOAc, NaOAc, KOAc, CsOAc, alkaline earth metal compounds such as $Ca(OH)_2$, $Ba(OH)_2$, $Mg(OH)_2$, $Sr(OH)_2$, $CaCO_3$, $BaCO_3$, $MgCO_3$, $SrCO_3$, $Ca(OAc)_2$, $Ba(OAc)_2$, $Mg(OAc)_2$, $Sr(OAc)$ 2, inorganic or organic basic compounds, for example halides, phenolates (such as Na phenolate), diphenolates, fluorides, phosphates, hydrogenphosphates and boranates of lithium, of sodium, of potassium, of caesium, of calcium, of barium and of magnesium, nitrogen bases and phosphorus bases such as, for example, tetramethylammonium hydroxide, tetramethylammonium acetate, tetramethylammonium fluoride, tetramethylammonium tetraphenylboranate, tetraphenylphosphonium fluoride, tetraphenylphosphonium tetraphenylboranate, dimethyldiphenylammonium hydroxide, tetraethylammonium hydroxide, DBU, DBN or guanidine systems such as, for example, 1,5,7-triazabicyclo[4.4.0]dec-5-ene, 7-phenyl-1,5,7-triazabicyclo[4.4.0]dec-5-ene, 7-methyl-1,5,7-triazabicyclo[4.4.0]dec-5-ene, 7,7'-hexylidenedi-1,5,7-triazabicyclo[4.4.0]dec-5-ene, 7,7'-decylidenedi-1,5,7-triazabicyclo[4.4.0]dec-5-ene, 7,7'-dodecylidenedi-1,5,7-triazabicyclo[4.4.0]dec-5-ene or phosphazenes such as, for example, the phosphazene base P1-t-oct=tert-octyliminotris(dimethylamino)phosphorane, phosphazene base P1-t-butyl=tert-butyliminotris(dimethylamino)phosphorane, BEMP=2-tert-butylimino-2-diethylamino-1,3-dimethylperhydro-1,3,2-diaza-2-phosphorane. Additionally tetramethylammonium hydroxide, tetramethylammonium acetate, tetramethylammonium fluoride, tetramethylammonium tetraphenylboranate, dimethyldiphenylammonium hydroxide, tetraethylammonium hydroxide, cetyltrimethylammonium tetraphenylboranate and cetyltrimethylammonium phenolate. Also suitable are phosphonium catalysts of formula (8):

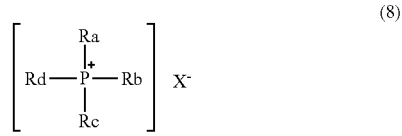

where Ra, Rb, Rc and Rd can be the same or different C1-C10-alkyls, C6-C4-aryls, C7-C15-arylalkyls or C5-C6-cycloalkyls, preferably methyl or C6-C14-aryls, particularly preferably methyl or phenyl, and X— can be an anion such as hydroxide, sulfate, hydrogensulfate, hydrogencarbonate, carbonate or a halide, preferably chloride or an alkylate or arylate of formula —OR, where R can be a C6-C14-aryl, C7-C15-arylalkyl or C5-C6-cycloalkyl, preferably phenyl. In addition, transesterification catalysts such as titanium alkoxides, such as titanium tetrabutoxide, tertiary amines, such as triethylamine, DMF, dimethylacetamide, methylpyrrolidone, tetramethylurea, dimethylimidazolidone hexaalkylguanidium halogens can. Additionally $AlCl_3$, $FeCl_3$, $BiCl_3$, $GaCl_3$, $SbCl_5$, $BF_3$, $Bi(OTf)_3$, $TiCl_4$, $ZrCl_4$, $TiB_4$ or $ZrBr_4$. Preferred catalysts are tetraphenylphosphonium chloride, tetraphenylphosphonium hydroxide, tetraphenylphosphonium phenolate, sodium phenolate and 4-dimethylaminopyridine; among these tetraphenylphosphonium phenolate is particularly preferred. The catalysts may also be used in any desired combination (two or more) with one another. Co-catalysts may in particular additionally also be used in order to increase the rate of the transesterification. These include, for example, the abovementioned alkaline salts of the alkali metals and/or alkaline earth metals.

These catalysts are preferably used in amounts of $10^{-2}$ to $10^{-8}$ mol, based one 1 mol of the cycloaliphatic dicarboxylic acid. The amounts of alkaline salts as co-catalyst can be in the range from 1 to 500 ppb, preferably 5 to 300 ppb and particularly preferably 5 to 200 ppb, based on 1 mol of the cycloaliphatic dicarboxylic acid.

The reaction of method step (i) is preferably conducted at temperatures from 180 to 280° C. Here, this temperature is preferably established or maintained in method steps (ib) to (id), if present.

In method step (ii) according to the invention, the cycloaliphatic diester of formula (Ia) or (Ib) is separated from the mixture of method step (i) by means of distillation. The term "distillation" is known per se to those skilled in the art as a thermal separation process. The separating action of distillation is based on the unequal distribution of the components over the gas and liquid phase at established thermodynamic equilibrium. Distillation is particularly suitable when the boiling points of the liquids to be separated are different or when the liquids have different vapour pressures at the same temperature. Those skilled in the art know how to conduct such a separation via distillation and how the corresponding apparatuses need to be embodied taking into account the deviations from the ideal thermodynamic equilibrium.

In particular, the term distillation is understood to include the processes of rectification, fractional distillation, vacuum distillation or azeotropic distillation and any desired combinations among these processes or with other thermal separation processes, for example adsorption/desorption processes and stripping. Possibilities for stepping up the process, for example by using dividing wall columns, reactive dividing wall columns, or the possibility of reactive distillation, are known to those skilled in the art.

It is preferred according to the invention that the distillation in method step (ii) is conducted at pressures of 10 mbar or less, preferably at <5 mbar, especially preferably at 4 mbar to 0.001 mbar, very particularly preferably at 2 mbar to 0.01 mbar. This has the advantage that the thermal stress on the product is kept as low as possible and thus undesired decomposition and side reactions can be minimized.

It is also preferred according to the invention that the distillation in method step (ii) is conducted at a temperature of 180° C. to 280° C., especially preferably at 200° C. to 260° C., very particularly preferably at 201° C. to 260° C. This temperature range is preferably to be combined with the abovementioned pressure in order to further minimize the undesired decomposition and side reactions. Since mass loss was observed in thermogravimetric analysis for cyclohexane-1,4-dicarboxylic acid already at temperatures above 200° C., it was especially surprising that the distillation according to the invention at these temperatures is associated with high yields and high purity.

According to the invention, method steps (i) and (ii) are preferably both conducted in the absence of an additional organic solvent. This does not exclude, according to the invention, that both the at least one carbonate used and the condensation product of the reaction formed can be present as solvent in these reaction steps (where possible). This is the case in particular if the carbonate is used in a stoichiometric excess with respect to the dicarboxylic acid. This preferred method variant is particularly gentle. However, according to the invention it is preferred that no additional organic solvent is added to the method. Method steps (i) and (ii) are especially preferably conducted in the absence of methylene chloride, methanol and toluene. As a result of the absence of an additional organic solvent, the method can be conducted favourably and in an environmentally friendly manner.

In another aspect of the present invention, a cycloaliphatic diester of formula (Ia) or (Ib) is provided,

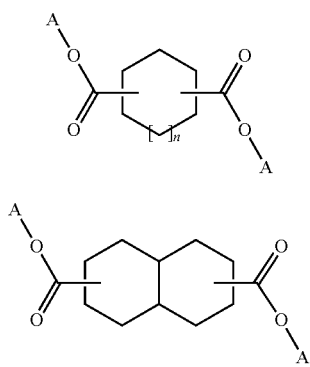

in which

A each independently is an aliphatic or aromatic radical and n is a number between 0 and 3, characterized in that the cycloaliphatic diester is obtained by the method according to the invention in all of the configurations and preferences described above. The examples according to the invention prove that, with the cycloaliphatic diester produced by the method according to the invention, other polymers with improved properties are obtained than with a cycloaliphatic diester that was not purified. In the comparative examples, polymers are obtained that have an intrinsically poorer colour, even after precipitation. This means that the corresponding diesters have a different spectrum of by-products than the diesters according to the invention. Some of these by-products of the comparative diesters are incorporated into the polymer chain. With the diesters according to the invention, in contrast, polymers could be obtained which have improved colour values, even though the diesters were exposed, according to the invention, to longer thermal stresses by the distillation. This is especially surprising since the purification method of the distillation was not commonly used or customary in the present technical field, as it was known practice to expose the cycloaliphatic diacids to as little thermal stress as possible, since otherwise decomposition and by-product reactions are expected.

In a further aspect of the present invention, a method for producing a polyestercarbonate by means of melt transesterification is provided, comprising the steps of:

(a) providing a cycloaliphatic diester of formula (Ia) or (Ib) by the method according to the invention in all of the configurations and preferences described above and (b) reacting the cycloaliphatic diester of formula (Ia) or (Ib) from method step (a), at least one dihydroxy compound and at least one diaryl carbonate in a melt transesterification process.

Here, the reaction in method step (b) is effected under conditions that are suitable for achieving an esterification. For example, condensation catalysts known to those skilled in the art can be used, for example alkali metal compounds, alkaline earth metal compounds, quaternary ammonium compounds, quaternary phosphonium compounds and any desired combinations thereof. The reaction conditions of the melt transesterification are likewise not particularly limited, as long as they are suitable for producing a corresponding polyestercarbonate. By way of example, the reaction temperature can be in the range of 100° C. to 350° C., preferably 180° C. to 310° C. The pressure can in particular be reduced in the later course of the method. The reaction time can vary between 1 h to 10 h. The polymerization can be conducted here in one or more stages, as known from the prior art.

As already described above, by means of this method according to the invention for producing a polyestercarbonate, polymers were surprisingly obtained which have a good intrinsic inherent colour.

It is especially advantageous according to the invention if method step (b) is performed immediately after method step (a). In this case the expression "immediately" is to be understood to mean that after the production of the diester according to the invention and the distillation thereof, the product obtained from the distillation is put into the melt transesterification process. As a result, the product may need to be only partially condensed, or the thermal energy may need to be only partially removed therefrom, since in the melt transesterification process a molten product is required. The thermal energy thus does not need to be applied twice. It is likewise possible for the heat accumulated in the condensation of the distilled product to be supplied to the melt transesterification process via suitable means, in order to thus design an economical and environmentally friendly method.

The at least one dihydroxy compound in method step (b) is preferably selected from the group consisting of cyclohexane-1,2-diol, cyclohexane-1,3-diol, cyclohexane-1,4-diol, cyclohexane-1,2-dimethanol, cyclohexane-1,3-dimethanol, cyclohexane-1,4-dimethanol, tricyclodecanedimethanol, 3,9-bis(1,1-dimethyl-2-hydroxyethyl)-2,4,8,10-tetraoxaspiro[5.5]undecane, 2,2-bis(4-hydroxycyclohexyl)propane, tetrahydro-2,5-furandimethanol, bisphenol A, 1,1-bis(4-hydroxyphenyl)-3,3,5-trimethylcyclohexane, 4,4'-dihydroxybiphenyl (DOD), 4,4'-dihydroxybiphenyl ether (DOD ether), bisphenol B, bisphenol M, the bisphenols (1) to (II)

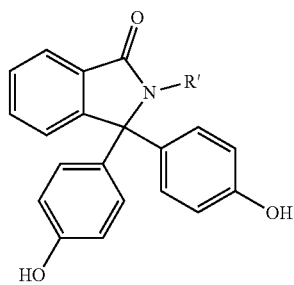

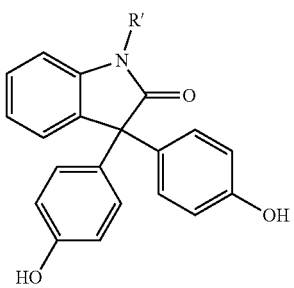

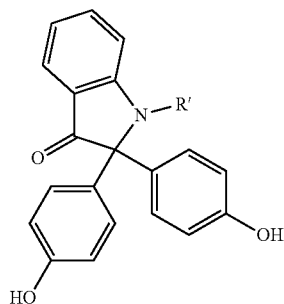

(III)

where in the formulae (I) to (III) R' in each case is $C_1$-$C_4$-alkyl, aralkyl or aryl, preferably methyl or phenyl, very particularly preferably methyl, butanediol, succinic acid, adipic acid, ethylene glycol, lactic acid, hexanediol and 1,4:3,6-dianhydrohexitols such as isomannide, isoidide and isosorbide. These are also known as 1,4:3,6-dianhydro-D-glycidol, 1,4:3,6-dianhydro-L-iditol and 1,4:3,6-dianhydro-D-mannitol. Particular preference is given here to aliphatic dihydroxy compounds. In one embodiment here, in addition to the aliphatic dihydroxy compound(s), an aromatic dihydroxy compound can be used in a molar deficiency.

The dihydroxy compound is very particularly preferably a 1,4:3,6-dianhydrohexitol such as isomannide, isoidide and isosorbide and among these most preferably isosorbide. It is also possible to use any desired mixtures. The dihydroxy compound is likewise preferably a mixture of 1,4:3,6-dianhydrohexitols such as isomannide, isoidide and isosorbide and at least one from the group consisting of cyclohexane-1,2-dimethanol, cyclohexane-1,3-dimethanol and/or cyclohexane-1,4-dimethanol. In this case it is especially preferred that the cyclohexane-1,2-dimethanol, cyclohexane-1,3-dimethanol and/or cyclohexane-1,4-dimethanol is used in amounts of up to 20%, preferably 1 to 10%, based on the total mass of the dihydroxy compounds.

It is likewise preferred that as diaryl carbonate in method step (b) a compound of formula (2) is used

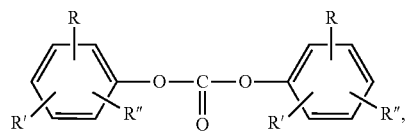

(2)

where R, R' and R" each independently can be the same or different and are hydrogen, optionally branched C1-C34-alkyl, C7-C34-alkylaryl or C6-C34-aryl, R can additionally also denote —COO—R''', where R''' is optionally branched C1-C34-alkyl, C7-C34-alkylaryl or C6-C34-aryl. The preferences already described with respect to formula (2) apply here as well. It has proved to be advantageous here to produce the cycloaliphatic diester according to the invention with the carbonate—by way of example DPC—that is also used to produce the polymer in method step (b). Small traces of the exemplary DPC in that case interfere in method step (b), as the DPC is then added in any case in method step (b). Therefore, this production method using DPC is very advantageous. Otherwise, all reagents and by-products must be very precisely removed prior to the polymerization.

According to the invention, therefore, a use of a cycloaliphatic diester of formula (Ia) or (Ib) is also provided,

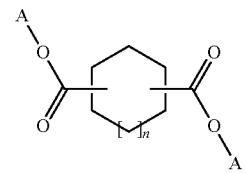

(Ia)

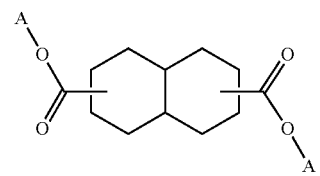

(Ib)

in which A and n have the above-described meanings in all combinations and preferences, for producing a polyestercarbonate by means of melt transesterification by the reaction of the cycloaliphatic diester with a bio-based dihydroxy compound, preferably a 1,4:3,6-dianhydrohexitol such as isomannide, isoidide and isosorbide, and a diaryl carbonate, characterized in that the cycloaliphatic diester of formula (Ia) or (Ib) is obtained by the reaction of at least one cycloaliphatic dicarboxylic acid and at least one aliphatic and/or aromatic carbonate in the presence of a basic catalyst. The configurations and preferences described with respect to the method according to the invention apply here in all combinations.

In a further aspect of the invention, a polyestercarbonate is provided which is obtained by the method according to the invention for producing a polyestercarbonate by means of transesterification process in all of the configurations and preferences described above. The polymers according to the invention surprisingly have a lower content of incorporated colour-imparting impurities.

EXAMPLES

Materials Used:
Cyclohexanedicarboxylic acid: cyclohexane-1,4-dicarboxylic acid; CAS 1076-97-7, 99%; Sigma-Aldrich, Munich, Germany Diphenyl carbonate: diphenyl carbonate, 99.5%, CAS 102-09-0; Acros Organics, Geel, Belgium Sodium phenolate: sodium phenolate trihydrate, 98%, CAS 652-67-5; Merck, Darmstadt, Germany Tetraphenylphosphonium phenolate: tetraphenylphosphonium phenolate, 66.5%, CAS 15464-47-8; Rheinchemie Tetramethylammonium hydroxide: tetramethylammonium hydroxide pentahydrate; ≥97% (CAS: 10424-65-4); Sigma-Aldrich, Munich, Germany 4-Dimethylaminopyridine: 4-(dimethylaminopyridine; ≥98.0%; purum; CAS 1122-58-3; Sigma-Aldrich, Munich, Germany Isosorbide: isosorbide (CAS: 652-67-5), 98%, Sigma-Aldrich, Munich, Germany; the isosorbide is recrystallized from isopropanol prior to use.

Irganox® B900 (Manufacturer: BASF)
Analytical Methods:
Determination of the Glass Transition Temperature:
The glass transition temperature is determined by means of differential scanning calorimetry (DSC) according to standard DIN EN ISO 11357-1:2009-10 and ISO 11357-2: 2013-05 at a heating rate of 10 K/min under nitrogen with determination of the glass transition temperature (Tg) measured as the point of inflection in the second heating run.

Chemical Characterization:

$^1$H NMR: 600 MHz; Bruker AV III HD 600 Spectrometer; solvent: $CDCl_3$

The molecular weight (Mn) of the polymer samples is estimated via the NMR spectrum (via the phenyl end group content).

Measurement of the Yellowness Index (YI):

For measurement of the yellowness index, a solution of the corresponding polymer or reactant was made up in dichloromethane (dichloromethane; Uvasol from Merck). To this end, a concentration of 0.02 g of polymer or reactant/ml was used. Each solution was filled into a glass cuvette (1 cm path length). The cuvette was measured in a Shimadzu UV1800 in transmission and the yellowness index (YI) for illuminant D 65 and 10° standard observer determined via the measurement of the colour coordinates (CIE) and calculated according to ASTM E313-10. This involved subtracting the measured value of the pure solvent from the measurement results of the respective samples.

Example 1

3.44 g (0.0199 mol) of cyclohexane-1,4-dicarboxylic acid and 8.99 g (0.0419 mol) of diphenyl carbonate and also 0.0031 g (0.0000182 mol) of sodium phenolate trihydrate were initially charged in a flask with short-path separator. The mixture was freed of oxygen by evacuating and purging with nitrogen four times. The mixture was melted and heated to 280° C. while stirring. The pressure was left at standard pressure. The mixture was stirred for 5 hours and in the process phenol was continuously distilled off.

Crude product 5.9 g of brown resin; NMR (1H NMR) confirmed obtention of the desired compound.

The example shows that in principle it is possible to operate at relatively high temperatures as well. However, it is preferable to operate under vacuum and at relatively low temperature, since the reaction proceeds more gently.

Example 2

3.44 g (0.0199 mol) of cyclohexane-1,4-dicarboxylic acid and 8.99 g (0.0419 mol) of diphenyl carbonate were initially charged in a flask with short-path separator. The mixture was freed of oxygen by evacuating and purging with nitrogen four times. The mixture was melted and heated to 160° C. while stirring. The pressure was adjusted to ambient pressure. The mixture is stirred for 30 minutes; thereafter the pressure is reduced to 10 mbar. The mixture was distilled off continuously for 30 minutes, during which time the pressure was lowered to 0.5 mbar.

Bottoms product: 3.9 g
Distillation receiver: 6.4 g

TLC analysis showed that the bottoms product was exclusively diphenyl carbonate and cyclohexanedicarboxylic acid. The distillation product was exclusively diphenyl carbonate. It was thus possible to show that under the selected conditions the desired product cannot be obtained.

Example 3

20 g (0.116 mol) of cyclohexane-1,4-dicarboxylic acid and 52.18 g (0.243 mol) of diphenyl carbonate and also 0.018 g (1.06*10-4 mol) of sodium phenolate trihydrate and 0.0072 g (0.01 wt. % based on the sum total of DPC and aliphatic diacid) of Irganox B900 were initially charged in a flask with short-path separator and vacuum valve adapter. The mixture was freed of oxygen by evacuating and purging with nitrogen four times. The mixture was melted and heated to 220° C. while stirring, and fractionally distilled. The pressure was adjusted to 600 mbar. The mixture was stirred for 60 minutes; thereafter the pressure was reduced to approximately 4 mbar (fractions 1 and 2 were removed).

Fraction 3 was withdrawn between 4.0 and 1.6 mbar and the 4th fraction was distilled off at 240° C. in the range from 1.5 to 0.9 mbar.

Bottoms residue: 5.9 g
Fraction 1: 15.3 g
Fraction 2: 7.1 g
Fraction 3: 6.0 g
Fraction 4: 23.5 g (62% of theoretical yield); fractions 3+4 (78% of theoretical yield)

TLC showed that exclusively phenol had been distilled off with fractions 1 and 2.

Fraction 3 contained the reaction product and traces of both DPC and phenol.

The desired product could be obtained in high purity in fraction 4. A white, transparent solid was obtained.

Example 4

3.44 g (0.0199 mol) of cyclohexane-1,4-dicarboxylic acid and 8.99 g (0.0419 mol) of diphenyl carbonate were initially charged in a flask with short-path separator. The mixture was freed of oxygen by evacuating and purging with nitrogen four times. The mixture was melted and heated to 180° C. while stirring. The pressure was adjusted to 600 mbar. The mixture was stirred for 60 minutes; thereafter the pressure was reduced to 10 mbar. DPC was distilled off continuously for 30 minutes, wherein the pressure was lowered in this time to 5 mbar.

Bottoms residue: 4.67 g
Distillation receiver: 8.0 g

TLC showed that exclusively DPC had been distilled off, the desired product could not be obtained.

Example 5

34.4 g (0.199 mol) of cyclohexane-1,4-dicarboxylic acid and 89.9 g (0.419 mol) of diphenyl carbonate and also 0.031 g (0.00027 mol) of sodium phenolate trihydrate were initially charged in a flask with short-path separator. The mixture was freed of oxygen by evacuating and purging with nitrogen four times. The mixture was melted and heated to 230° C. while stirring. The mixture was stirred under standard pressure at 230° C. for 3 hours; phenol distilled off in the process. Thereafter, the temperature of the reaction melt was reduced to 200° C. and the pressure reduced to 500 mbar. Phenol continued to distil off in the process.

The mixture was stirred for an hour and the pressure was reduced continuously down to 5 mbar at the same time. The volatile constituents were continuously removed. The temperature was raised to 210° C. and the vacuum reduced to 1 mbar. Distillation was effected until volatile constituents were no longer drawn off and the overhead temperature fell considerably. The distillation receiver was changed, the temperature was raised to 220° C. and the vacuum reduced to 0.5 mbar. The product distilled in the process. The mixture was distilled for 30 minutes; the overhead temperature rose

Example 6

Test according to example 2 of JP H07-126213

16.6 g (0.096 mol) of cyclohexane-1,4-dicarboxylic acid, 45.0 g (0.21 mol) of diphenyl carbonate and also 0.09 g of 4-dimethylaminopyridine were initially charged in a three-neck flask with short-path separator. The apparatus was freed of oxygen by evacuating and purging with nitrogen four times. The mixture was melted at 180° C. and heated to 220° C. while stirring. The pressure was reduced within 45 minutes to 700 mbar and then reduced within a further 45 minutes to 2 mbar. Phenol was continuously removed in the process.

The product was withdrawn. This yields a grey-white powder. NMR analysis showed the desired product. Yield: 17.5 g. The product was used further without purification.

Example 7

Test according to example 4 of WO0210111

4.65 g (0.027 mol) of cyclohexane-1,4-dicarboxylic acid, 17.6 g (0.082 mol) of diphenyl carbonate and also 0.3 g of a 24% solution of tetramethylammonium hydroxide solution in water (approximately 0.0008 mol) were initially charged in a three-neck flask with short-path separator. The apparatus was freed of oxygen by evacuating and purging with nitrogen four times. The mixture was melted at 180° C. and heated to 210° C. while stirring. The reaction mixture was stirred at this temperature for 4.5 hours. The temperature was then lowered to 150° C. and the pressure lowered to 2 mbar. Stirring was effected for an hour and phenol was continuously removed.

The product was withdrawn. This yielded a grey-beige powder. NMR (1H NMR) confirmed the desired product. Yield: 20.3 g

Example 8

32.2 g (0.187 mol) of cyclohexane-1,4-dicarboxylic acid, 210.0 g (0.980 mol) of diphenyl carbonate and also 0.18 g of 4-dimethylaminopyridine were initially charged in a three-neck flask with short-path separator. The apparatus was freed of oxygen by evacuating and purging with nitrogen four times. The mixture was melted at 180° C. and heated to 220° C. while stirring. The pressure was reduced within approximately 60 minutes to 700 mbar and then reduced within a further 4 hours to 10 mbar. Phenol was continuously removed in the process. The pressure was reduced within 50 minutes to 15 mbar; volatile constituents were removed in the process. The pressure was reduced within 30 minutes to 1.5 mbar.

For distillation of the product, the temperature was lowered to 210 to 215° C. and the pressure lowered to 1 mbar. The product fraction was taken off under these conditions.

The product was withdrawn. This yielded a white solid (yield 43 g; 71% of theory).

TABLE 1

| Optical data (YI) | |
| --- | --- |
| Product from example | YI |
| 5 | 0.07 |
| 6 | 17.67 |
| 7 | 1.18 |
| 8 | 0.0 |

The optical data show that the distillation of each product lead to a diester having better optical quality.

Polymerization of Diphenyl Cyclohexanedicarboxylate with Isosorbide.

Example A 8.00 g (0.0246 mol) of diphenyl cyclohexane-1,4-dicarboxylate from example 5 and 8.98 g (0.0616 mol) of isosorbide and also 8.30 g (0.0387 mol) of diphenyl carbonate were initially charged in a flask with short-path separator. 50 ppm of caesium carbonate and 50 ppm of sodium hydroxide (aqueous solution of sodium hydroxide in water; 6.5%) were added. The flask was freed of oxygen by evacuating and purging with nitrogen four times. The reaction mixture was melted at 190° C. and the pressure reduced carefully within approximately 15 minutes to 200 mbar. The reaction mixture was stirred for 20 minutes. The pressure was reduced to 100 mbar and the temperature raised to 210° C. The mixture was stirred for 30 minutes under these conditions, wherein phenol was continuously removed from the reaction mixture. The pressure was reduced to 10 mbar and reduced after a further 10 minutes to 2 mbar. The reaction mixture was stirred for another 15 minutes at 2 mbar. Thereafter, the product was withdrawn, dissolved in dichloromethane (the product was completely soluble in dichloromethane) and precipitated in methanol. This yielded a white powder.

Example B

The method was conducted as in example A. The product from example 8 was used as reactant.

Example C

The method was conducted as in example A. The product from example 7 was used as reactant.

Example D

The method was conducted as in example A. The product from example 6 was used as reactant.

TABLE 2

| Optical measurement (after precipitation) | | | |
| --- | --- | --- | --- |
| Example | Tg [° C.] | Mn (NMR) [g/mol] | YI |
| A | 131 | approximately 5000 | 7.9 |
| B | 141 | approximately 11 000 | 7.06 |
| C | 131 | approximately 7000 | 12.4 |
| D | 135 | approximately 5700 | 19.8 |

The brightness and intrinsic inherent colour are an essential quality characteristic of polymers. The inherent colour of the polymers is normally caused by low molecular weight products. These products are formed during the polycondensation and are generally not incorporated into the polymer chain. These impurities can in general be removed by precipitating the polymer. However, it has surprisingly been found that the products purified by distillation result, after precipitation, in a lesser inherent colour of the polymer. This means that in the non-distilled comparative samples an incorporation of the colour-imparting products into the polymer chain has taken place, whereas in the diaryl esters according to the invention such an incorporation can be reduced.

The invention claimed is:

1. A method for producing a cycloaliphatic diester of formula (Ia) or (Ib),

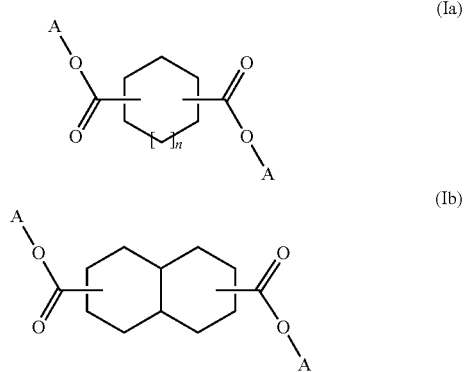

in which
A each independently is an aliphatic or aromatic radical and
n is a number between 0 and 3,
comprising the steps of
(i) reacting a mixture comprising at least one cycloaliphatic dicarboxylic acid and at least one aliphatic and/or aromatic carbonate, in the presence of a basic catalyst, to give a cycloaliphatic diester of formula (Ia) or (Ib) and
(ii) separating the cycloaliphatic diester of formula (Ia) or (Ib) from the mixture of method step (i) by means of distillation at a temperature of 180° C. to 280° C.

2. The method according to claim 1, wherein the distillation in method step (ii) is conducted at pressures of 10 mbar or lower.

3. The method according to claim 1, wherein, in method step (i), an aromatic carbonate of formula (2) is used

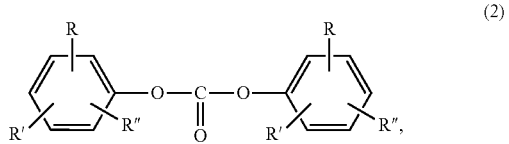

where R, R' and R" each independently can be the same or different and are hydrogen, optionally branched C1-C34-alkyl, C7-C34-alkylaryl or C6-C34-aryl, R can additionally also denote —COO—R'", where R'" is optionally branched C1-C34-alkyl, C7-C34-alkylaryl or C6-C34-aryl.

4. The method according to claim 3, wherein, in method step (i), diphenyl carbonate is used as aromatic carbonate.

5. The method according to claim 1, wherein method steps (i) and (ii) are conducted in the absence of an additional organic solvent.

6. The method according to claim 1, wherein, in method step (i), at least one stabilizer selected from the group consisting of P-containing stabilizers and/or phenolic free-radical scavengers is added.

7. The method according to claim 1, wherein the reaction of method step (i) is conducted at temperatures of 180 to 280° C.

8. The method according to claim 1, wherein, during the reaction in method step (i), the volatile constituents which have a boiling point below the cycloaliphatic diester of formula (Ia) or (Ib) and below the aliphatic and/or aromatic carbonate are removed, optionally in steps, by means of distillation.

9. A method for producing a polyestercarbonate by means of melt transesterification, comprising the steps of:
(a) producing a cycloaliphatic diester of formula (Ia) or (Ib),

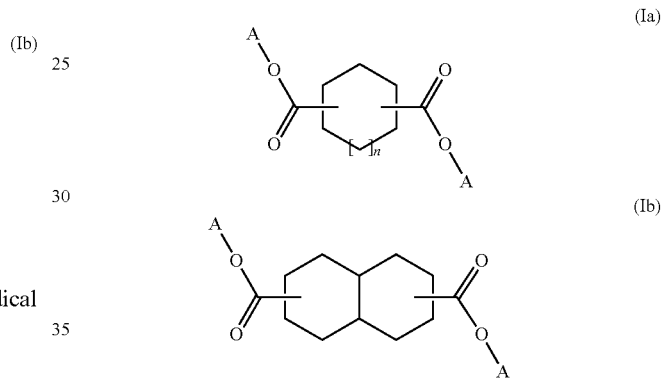

in which
A each independently is an aliphatic or aromatic radical and
n is a number between 0 and 3,
by:
(i) reacting a mixture comprising at least one cycloaliphatic dicarboxylic acid and at least one aliphatic and/or aromatic carbonate, in the presence of a basic catalyst, to give the cycloaliphatic diester of formula (Ia) or (Ib); and
(ii) separating the cycloaliphatic diester of formula (Ia) or (Ib) from the mixture of method step (i) by means of distillation at a temperature of 180° C. to 280° C.; and
(b) reacting the cycloaliphatic diester of formula (Ia) or (Ib) from method step (a), at least one dihydroxy compound and at least one diaryl carbonate in a melt transesterification process.

10. The method according to claim 9, wherein method step (b) is performed immediately after method step (a).

11. The method according to claim 9, wherein the dihydroxy compound in method step (b) is selected from the group consisting of cyclohexane-1,2-diol, cyclohexane-1,3-diol, cyclohexane-1,4-diol, cyclohexane-1,2-dimethanol, cyclohexane-1,3-dimethanol, cyclohexane-1,4-dimethanol, tricyclodecanedimethanol, 3,9-bis(1,1-dimethyl-2-hydroxyethyl)-2,4,8,10-tetraoxaspiro [5.5] undecane, 2,2-bis(4-hydroxycyclohexyl)propane, tetrahydro-2,5-furandimethanol, bisphenol A, 1,1-bis(4-hydroxyphenyl)-3,3,5-trimethylcyclohexane, 4,4'-dihydroxybiphenyl (DOD), 4,4'-dihydroxybiphenyl ether (DOD ether), bisphenol B, bisphenol M, the bisphenols (I) to (III)

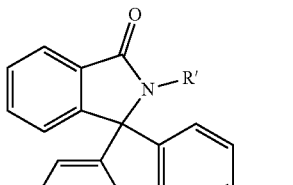
(I)

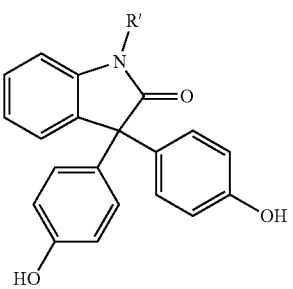
(II)

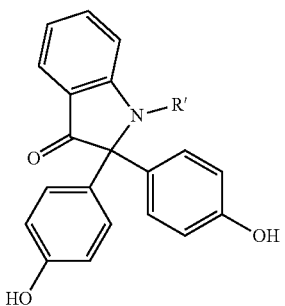
(III)

wherein the formula (I) to (III) R' in each case is C1-C4-alkyl, aralkyl or aryl, butanediol, succinic acid, adipic acid, ethylene glycol, lactic acid, hexanediol and 1,4:3,6-dianhydrohexitols.

12. A method according to claim 9, wherein as diaryl carbonate in method step (b) a compound of formula (2) is used

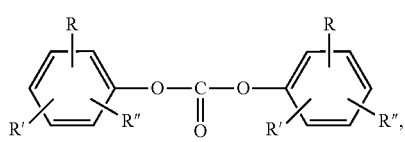
(2)

where R, R' and R'' each independently can be the same or different and are hydrogen, optionally branched C1-C34-alkyl, C7-C34-alkylaryl or C6-C34-aryl, R can additionally also denote —COO—R''', where R''' is optionally branched C1-C34-alkyl, C7-C34-alkylaryl or C6-C34-aryl.

13. A method of producing a polyestercarbonate by means of melt transesterification comprising:
(a) producing a cycloaliphatic diester of formula (Ia) or (Ib),

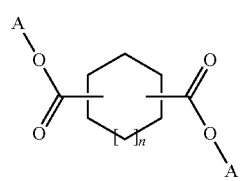
(Ia)

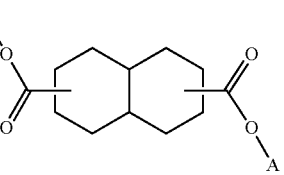
(Ib)

in which
A each independently is an aliphatic or aromatic radical and
n is a number between 0 and 3,
by:
(i) reacting a mixture comprising at least one cycloaliphatic dicarboxylic acid and at least one aliphatic and/or aromatic carbonate, in the presence of a basic catalyst, to give the cycloaliphatic diester of formula (Ia) or (Ib); and
(ii) separating the cycloaliphatic diester of formula (Ia) or (Ib) from the mixture of method step (i) by means of distillation at a temperature of 180° C. to 280° C.; and
(b) reacting the cycloaliphatic diester of formula (Ia) or (Ib) with a bio-based dihydroxy compound and a diaryl carbonate.

14. The method according to claim 11, wherein R' in each case is methyl or phenyl.

15. The method according to claim 11, wherein R' in each case is methyl.

16. The method according to claim 11, wherein the 1,4:3,6-dianhydrohexitol is selected from the group consisting of isomannide, isoidide and isosorbide.

17. The method according to claim 13, wherein the bio-based dihydroxy compound comprises a 1,4:3,6-dianhydrohexitol.

18. The method according to claim 17, wherein the 1,4:3,6-dianhydrohexitol is selected from the group consisting of isomannide, isoidide or isosorbide.

* * * * *